US006989271B2

(12) United States Patent
Dezawa et al.

(10) Patent No.: US 6,989,271 B2
(45) Date of Patent: Jan. 24, 2006

(54) SCHWANN CELLS ORIGINATING IN MYELOID INTERSTITIAL CELLS

(75) Inventors: Mari Dezawa, Yokosuka (JP); Hajime Sawada, Yokohama (JP); Masahiko Takano, Yokohama (JP)

(73) Assignee: Sanbio, Inc., Mountain View, CA (US)

( * ) Notice: Subject to any disclaimer, the term of this patent is extended or adjusted under 35 U.S.C. 154(b) by 0 days.

(21) Appl. No.: 10/481,603

(22) PCT Filed: Jun. 21, 2002

(86) PCT No.: PCT/JP02/06249

§ 371 (c)(1),
(2), (4) Date: Dec. 22, 2003

(87) PCT Pub. No.: WO03/000871

PCT Pub. Date: Jan. 3, 2003

(65) Prior Publication Data

US 2004/0197309 A1 Oct. 7, 2004

(30) Foreign Application Priority Data

Jun. 22, 2001 (JP) .............................. 2001-190251

(51) Int. Cl.
*C12N 5/00* (2006.01)
(52) U.S. Cl. ...................... 435/377; 435/372; 435/384; 435/392; 424/93.7
(58) Field of Classification Search ................ 435/372, 435/377, 378, 384, 392; 424/93.7
See application file for complete search history.

(56) References Cited

U.S. PATENT DOCUMENTS 5,714,385 A * 2/1998 Mather et al. .............. 435/406

6,576,237 B1 * 6/2003 Ingham et al. ........... 424/158.1
2003/0220280 A1 * 11/2003 Bunge et al. ................. 514/44

FOREIGN PATENT DOCUMENTS

WO      WO 96/35776      * 11/1996

OTHER PUBLICATIONS

National Institute of Neurological Disorders and Stroke (NINDS), "Angelman Syndrome Information Page" Dec. 2003, p. 1, accessed Oct. 15, 2004 http://www.ninds.nih-.gov/health_and_medical/disorders/angelman.htm.*
National Institute of Neurolocial Disorders and Stroke (NINDS), "Dementia With Lewy Bodies Information Page" Feb. 2002, p. 1, accessed Oct. 15, 2004 http://www.ninds.nih.gov/health_and_medical/disorders/dimentiawithlewybodies_doc.htm.*

(Continued)

Primary Examiner—Leon B. Lankford, Jr.
Assistant Examiner—Allison M. Ford
(74) Attorney, Agent, or Firm—Morrison & Foerster LLP

(57) ABSTRACT

There is provided a method of inducing bone marrow stromal cells to differentiate into bone marrow stromal cell-derived Schwann cells in vitro, comprising the steps of: collecting bone marrow stromal cells from bone marrow and culturing the cells in a standard essential culture medium supplemented with a serum; adding a reducing agent to the culture medium and further culturing the cells; adding a differentiation inducing agent to the culture medium and further culturing the cells; and adding a cyclic AMP-augmenting agent or a cyclic AMP analogue and/or a glial cell differentiation and survival stimulating factor to the culture medium, and further culturing the cells to obtain the bone marrow stromal cell-derived Schwann cells. There are also provided bone marrow stromal cell-derived Schwann cells obtained thereby and a pharmaceutical composition for neural regeneration that comprises them.

14 Claims, 17 Drawing Sheets

OTHER PUBLICATIONS

National Institute of Neurological Disorders and Stroke (NINDS), "Alzheimer's Disease Information Page" Sep. 2003, p. 1, accessed Oct. 15, 2004 http://www.ninds.hih.gov/health_and_medical/disorders/alzheimersdisease_doc.htm.*

Bosch et al, Journal of Neuroscience, 1989, vol. 9, No. 10, pp 3690-3698.*

Jasmin et al, Journal of Neuroscience, 2000, vol. 20, No. 24, pp 9215-9223.*

Bunge et al, U.S. Provisional Appl. No. 60/354,306, filed Feb. 7, 2002.*

M. Dezawa et al., "Sciatic Nerve Regeneration in Rats Induced by Transplantaion of in Vitro Differentiated Bone-Marrow Stromal Cells," European Jornal of Neuroscience, vol. 14, pp. 1771-1776, 2001.

G. Kopoen et al., "Marrow Stromal Cells Migrate Throughout Forebrain and Cerebellum, and They Differentiate Into Astrocytes After Injection Intoo Neonatal mouse Brains," Proc. Natl. Acad. Sci. , vol. 96, pp. 10711-10716, 1999.

J. Sanchez-Ramos, "Adult Bone Marrow Stromal Cells Differentiate Into Neural Cells in Vitro," Experimental Neurology, vol. 247-256, 2000.

D. Woodbury et al., "Adult Rat and Human Bone Marrow Stromal Cells Differentiate Into Neutrons," Journal of Neuroscience Research, vol. 364-370, 2000.

Martin E. Schwab et al. (1988) "Oligodendrocytes and CNS Myelin Are Nonpermissive Substrates for Neurite Growth and Fibroblast Spreading in vitro," *Journal of Neuroscience* 8(7); pp. 2381-2393.

S. Hall et al. (1989) "Electron Microscopic Study of the Interation of Axons and Glia at the Site of Anastomosis Between the Optic Nerve and Cellular or Acellular Sciatic Nerve Gratfts," *Journal of Neurocytology* 18 ; pp. 171-184.

Diane M. Snow et al. (1990) "Sulfated Proteoglycans in Astroglial Barriers Inhibit Neurite Outgrowth in Vitro," *Experimental Neurology* 109; pp. 111-130.

E. Blaugrund et al. (1992) "Disappearance of Astrocytes and Invasion of Macrophages Following Crush Injury of Adult Rodent Optic Nerves: Implications for Regeneration," *Experimental Neurology* 118; pp. 105-115.

Martin Bastmeyer et al. (1994) "Similarities and Differences Between Fish Oligodendrocytes and Schwann Cells in Vitro, " *GLIA* 11; pp. 300-314.

Manuel Vidal-Sanz et al. (1987) "Axonal Regeneration and Synapse Formation in the Superior Colliculus by Retinal Ganglion Cells in the Adult Rat," *Journal of Neruoscience* 7(9); pp. 2894-2909.

Mari Dezawa et al. (1997) "The Role of Schwann Cells During Retinal Ganglion Cell Regeneration Induced by Peripheral Nerve Transplantation," *Investigative Opthalmology & Visual Science* 38(7); pp. 1401-1410.

Albert J. Aguayo et al. (1983) "A Potential for Axonal Regeneration in Neurons of the Adult Mammalian Nervous System," *Birth Defects: Original Article Series* 19(4); pp. 327-340.

Maio S. Chen et al. (2000) "Nogo-A is a Myelin-Associated Neurite Outgrowth Inhibitor and an Antigen for Monoclonal Antibody IN-1," *Nature* 403 ; pp. 434-439.

M. Taito, professor, Tohoku University, "Studies in Establishing Differentiation Function-Maintaining Cell Lines and Using Them for Reconstruction of Biohistological Function," NEDO 1999 Teian Kobo Jigyo Seika Hokoku: 97S09-003.

Michael A. Chemousov et al. (1996) "Schwann Cells Secrete a Novel Collagen-like Adhesive Protein that Binds N-Syndecan," *The Journal of Biological Chemistry* 271(23) pp. 13844-13853.

* cited by examiner

Fig.2
Peripheral nerve system
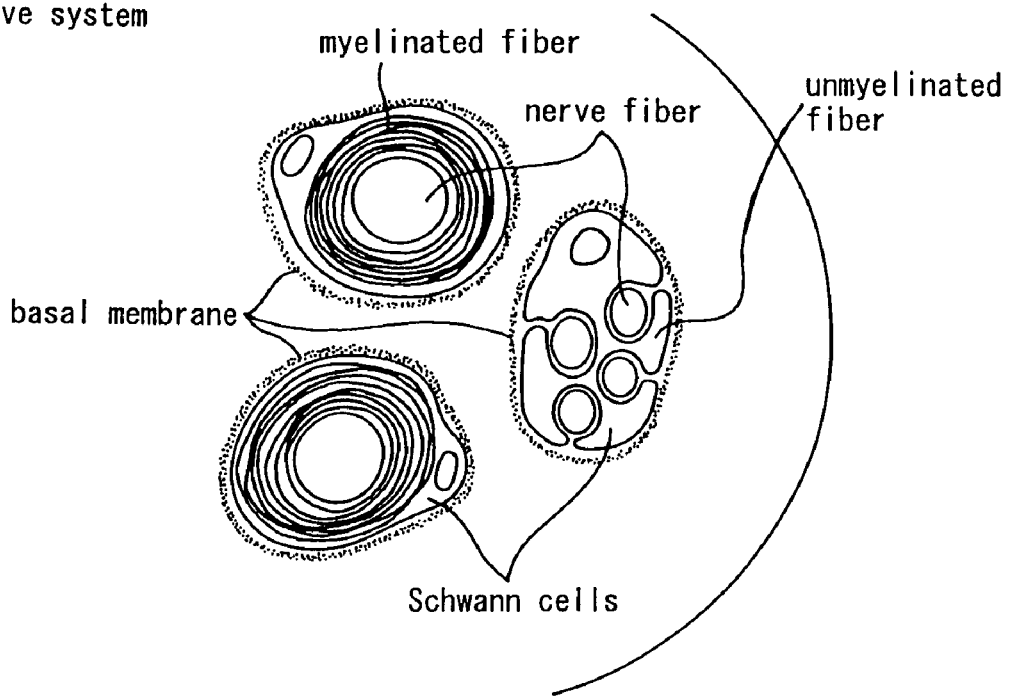
Optic nerve
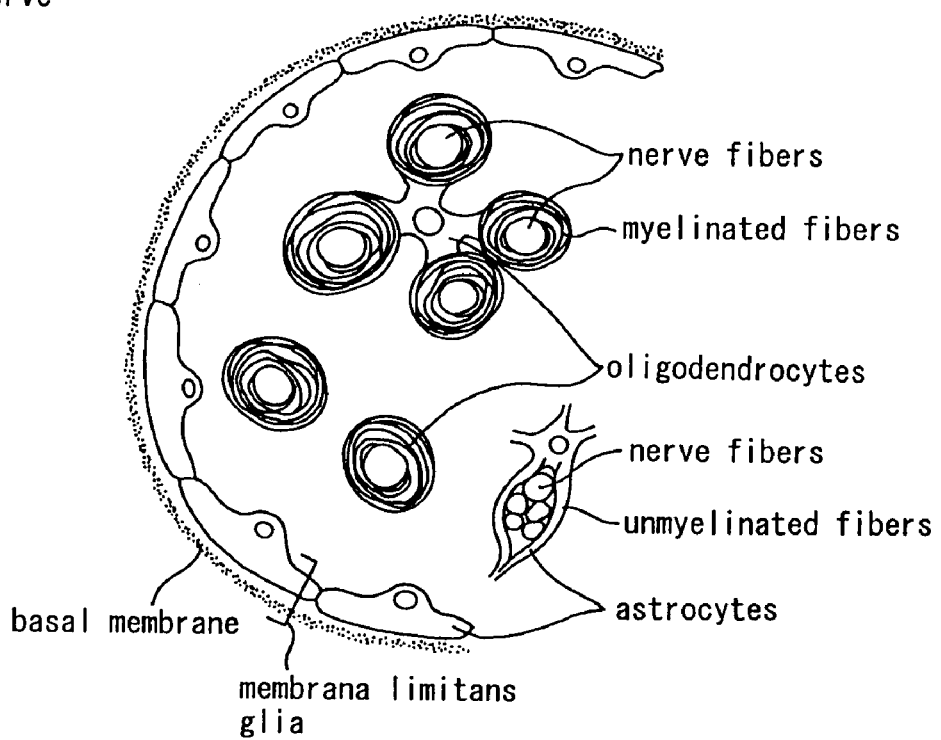

Fig.11

Collect and culture stromal cells from bone marrow of adult rats (Wistar strain)

↓

After 4 passages

↓

At subconfluency,
αMEM, 20%FCS, b-mercaptoethanol (1mM)

↓ (24 hrs)

αMEM, 20%FCS, retinoic acid (35ng/ml)

↓ (3 days)

αMEM, 20%FCS, forskolin(5μM),
PDGF(5ng/ml), bFGF(10ng/ml),
neuregulin(200ng/ml)

↙ (7 days) ↘

Immunostaining
p75, S-100,
GFAP, O4, Nestin,

1) Labeling of nuclei with Hoechst 33342 followed by trypsin treatment,

2) Mixing with Matriegel, packing into hollow fiber

↙ ↘

Peripheral nerve regeneration
Transplantation into adult rat severed sciatic nerve Central nerve regeneration
Transplantation into adult rat severed optic nerve Fig.13
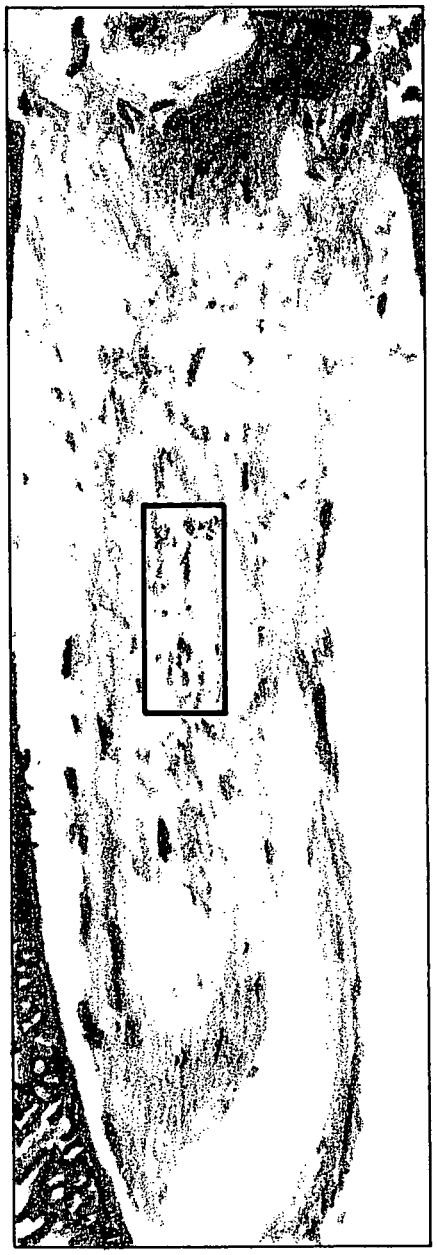
Optic nerve-3 weeks after MSC transplantation
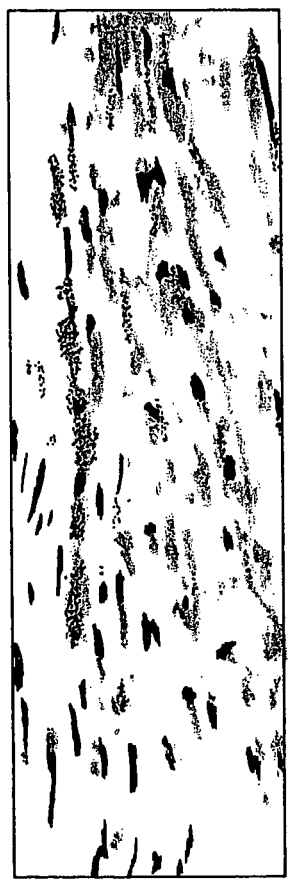
FITC:Cholera toxin    TexRed:Brd-U-MSC    Alexa633:MAG Transplantation into severed sciatic nerve
(7th day GAP43 labeling)

Fig.16
Sciatic nerve-4 weeks after MSC transplantation
 
GFP:MSC  Alexa633:MAG    Alexa546:Neurofilament
Fig.17
Sciatic nerve-4 weeks after MSC transplantation
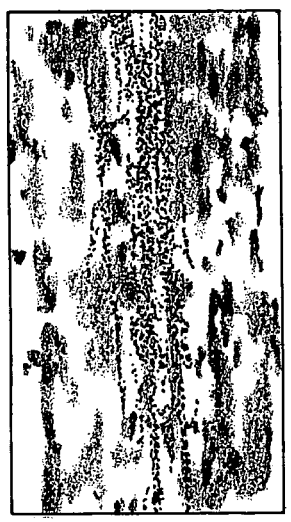 
GFP       :MSC            Alexa633:MAG
Alexa633:MAG              Alexa546:Neurofilament Fig.18
Sciatic nerve-4 weeks after MSC transplantation
GFP　　　：MSC
Alexa633：MAG
Alexa633：MAG
Alexa546：Neurofilament

SCHWANN CELLS ORIGINATING IN MYELOID INTERSTITIAL CELLS

TECHNICAL FIELD

The present invention relates to an in vitro method of inducing bone marrow stromal cells to differentiate into Schwann cells, to the bone marrow stromal cell-derived Schwann cells, to a pharmaceutical composition for neural regeneration that comprises them, and to a method for treatment of neural diseases using the Schwann cells and the composition.

BACKGROUND ART

Damage to the nervous system, and particularly the central nervous system including brain, spinal cord, and optic nerve is believed to be irreversible, leading ultimately to the process of degeneration. Traffic accidents and sports injuries, ischemia, tumors, prolonged inflammation, cryptogenic degenerative disease and the like are among the causes of neurological diseases which occur with a high incidence among the population, and are of urgent social significance.

The irreversibility of central nerve damage is attributed to the glial environment of nerve tissue. The brain and spinal cord have the same glial environment, which will now be described using the optic nerve as an example of a central nerve.

1) First, nerve fibers undergo degeneration and gradually disappear. During the process, the myelin sheaths covering the nerves also degenerate leaving cell residues (see FIG. 1b). The myelin sheaths formed by oligodendrocytes contain substances which strongly inhibit nerve fiber regeneration and elongation[1].

2) The astrocytes proliferate and enlarge, resulting in gliosis (see FIG. 1b). More specifically, they displace the nerve fibers, occupying the primary locations and thereby physically inhibiting regeneration[2]. The astrocytes forming the gliosis exhibit a morphology contrasting considerably with that of normal astrocytes, with a greater number of processes and intricately complex forms. Particularly in the case of injury, the site of damage shows numerous layers of astrocytes stacked orthogonally to the direction of extension of the nerve fibers and linked together at their processes, forming a cap-like barrier structure.

3) Processing of the oligodendrocytes and their cell residue substances such as myelin after degeneration is slower compared to other regenerating tissues such as peripheral nerve system. The main reason for this is presumably the very low degree of infiltration of peripheral immune cells such as macrophages and monocytes, resulting in delayed processing of the residue in the early stages.

The following explanations have been proposed for lack of regeneration of optic nerves.

1) As mentioned above, oligodendrocytes have a strong inhibiting effect on neural regeneration. Specifically, the molecule Nogo extracted from oligodendrocytes has been shown to be an inhibitor[1,9]. Experiments with culturing systems have shown that during extension of neurites, the processes contacting with the myelin sheaths of oligodendrocytes not only stop extending, but even regress (contact inhibition). Moreover, neurites do not extend at myelinated areas, and in culturing the processes grow to avoid them.

2) Gliotic astrocytes produce various inhibiting substances, including proteoglycans such as keratin sulfate and chondroitin sulfate[3].

3) The optic nerves and the entire central nervous system are exceedingly silent even after suffering injury. The system is not under immune surveillance, and this is instead considered to be a disadvantage for regeneration. For example, the peripheral nerve system described hereunder differs from the optic nerve even in the structure of the glia, and it has been compared and studied as a regenerating system even though it is composed of the same nerve tissue. Upon injury of peripheral nerve tissue, immune cells such as peripheral macrophages rapidly infiltrate (within a few hours to a couple of days) to process the cell residue. Meanwhile, cytokines are secreted in large amounts, promoting regeneration of the nerve tissue. Such neural regeneration occurs in concert with a cascade of phenomena with one reaction leading to another, but no infiltration of macrophages is seen in the optic nerve in the early stages. This has been attributed to the suppression of macrophage activity in the central nervous system including the optic nerve[4]. It appears that this suppressing function arose in order to prevent macrophage digestion of complex developed central neural nets. It has therefore been conjectured that it is the absence of the first trigger in the optic nerves that leads to degeneration instead of regeneration.

4) In order for regeneration to occur, a structural scaffolding is necessary to induce nerve fibers. However, once degeneration has occurred in the optic nerves, the route for regeneration is lost. In the optic nerves, each oligodendrocyte forms numerous myelin sheaths on the nerve fibers, and astrocytes surround the myelinated fibers and cover the unmyelinated fiber bundles (see FIG. 2, bottom). The basal membrane is present only outside of the astrocytes forming the membrana limitans glia, or in other words, the entire optic nerve may be considered to be inside a single basal membrane sheath. In the peripheral nerves, the basal membrane serves as a route for regeneration. Consequently, once the nerve fibers in the optic nerve have degenerated, the route which once existed for each of the nerve fibers is no longer present.

Yet peripheral nerves, unlike central nerves, are capable of regeneration.

Unlike central nerves, the primary cells of the peripheral nerves are Schwann cells. All of the nerve fibers, whether myelinated or unmyelinated, are covered with Schwann cells (see FIG. 2, top). Schwann cells are derived from neural crest cells, while the central glia (oligodendrocytes, astrocytes) which act inhibitorily on neural regeneration are derived from neural tubes, and therefore the sources of differentiation are different.

Peripheral nerves are believed to regenerate in the following fashion.

1) When injury such as a cut is suffered by peripheral nerves, Wallerian degeneration occurs at the peripheral end from the site of injury (see FIG. 3). The Schwann cells return to an undifferentiated state from the myelin-forming differentiated type, and are then activated to divide and proliferate, exhibiting a funicular form. In the peripheral nerves, the individual nerve fibers are independently surrounded by Schwann cells, with the outer area covered by a basal membrane (see FIG. 2). That is, each of the nerves resides within a separate basal membrane sheath. Thus even when degeneration occurs, the Schwann cells activated in the basal membrane sheath proliferate to form a funicular structure, thus providing a foothold for reconstruction of the neural network. Wallerian degeneration, therefore, is not degeneration in the strict sense but rather the first step toward regeneration.

2) Peripheral macrophages play a major role in the process of Wallerian degeneration. The macrophages infiltrate rapidly at the peripheral end of the site of injury, processing the remnants of the degenerated nerves fibers and myelin (see FIG. 3) while also secreting cytokines such as IL-1 to activate the Schwann cells. Although no definite conclusions can be drawn regarding the cause which induces filtration of macrophages, the Schwann cells themselves have been indicated as a likely candidate. In any case, it is believed that the Schwann cells activated by the macrophage signals synthesize various factors indispensable for regeneration, such as nerve growth factor which will be explained below, and guide regeneration of the nerve.

3) The myelin sheaths of Schwann cells have a low inhibitory effect. This is a major difference from the myelin of oligodendrocytes which does exhibit an inhibitory effect [5]. In addition, it is known that the composition of the myelin protein of Schwann cells and oligodendrocytes differs.

Thus, even when injured, the central glia do not revert back to their differentiated state to undergo differentiation and proliferation or significantly alter their form, as do the Schwann cells of the peripheral nerves, but instead maintain their relatively differentiated phenotype. The peripheral nerves on the other hand are characterized by exhibiting a rapid, highly flexible response to injury.

Schwann cells are considered to play the following role in neural regeneration.

Schwann cells produce numerous factors and secrete them in a diffuse manner. Moreover, their own cell membrane surfaces are covered with a basal membrane, and extracellular matrix components are included therein. Cell adhesion molecules are also known to be expressed in Schwann cell membranes, and it is thought that these factors act as a whole to induce neural regeneration (see FIG. 4).

1. Secreted Factors

Schwann cells are known to produce many neurotrophic factors, among which the following are the main ones involved in regeneration: 1) the neurotrophin family, including nerve growth factor, brain-derived neurotrophic factor, neurotrophin-3, neurotrophin-4/5; 2) ciliary neurotrophic factor; 3) the FGF family, including acidic and basic fibroblast growth factor; 4) the insulin family, including insulin-like growth factor-I and II; and 5) transforming growth fator-β2 and β3.

These neurotrophins have powerful effects not only on the survival of neurons but also on neurite elongation and the like. Other factors also have neurotrophic effects and neurite elongating effects on nerves, but their action mechanisms are considered to be autocrinic since they simultaneously activate the Schwann cells themselves.

2. Extracellular Matrix Components

These include fibronectin, laminin, type IV collagen and tenascin. Based on experiments with cultured systems, it is believed that fibronectin and laminin play a supporting role in neural regeneration.

3. Cell Adhesion Molecules

A large number of cell adhesion molecules have been identified. The following description will focus on those associated with Schwann cells and neural regeneration.

1) Immunoglobulin Superfamily

NCAM (Neural Cell Adhesion Molecule) and L1 are expressed on Schwann cell membranes and play important roles as adhesion molecules during elongation of the nerve fibers as they contact with the Schwann cell scaffolding. Both are connected to the cytoskeleton and function to maintain the shape of the cell, while also accomplishing intracellular activation through inositol phosphate system and calcium channel activation. In addition, MAG (Myelin Associated Glycoprotein) is expressed between Schwann cells after nerve elongation has progressed to some degree and remyelination of the nerve fibers has begun.

2) Cadherin Superfamily

Cadherins are calcium-dependent cell adhesion molecules of which numerous types have been identified. N-cadherin is associated particularly with neural regeneration. Like NCAM and L1 of the immunoglobulin superfamily, this molecule also plays an important role during elongation of the nerve fibers as they contact with and recognize Schwann cells.

3) Integrin Superfamily

Integrins are cellular receptors for the aforementioned extracellular matrix components. They are heterodimeric molecules composed of two subunits, α and β. Like cadherins, they are also thought to link with the cytoskeleton and function directly in signal transduction between cells. Schwann cells express the $\alpha_6\beta_4$ subtype which plays a role in the process of remyelination during regeneration.

Regeneration of central nerves has been attempted in the past several decades or so by numerous researchers. The following is a summary of those attempts.

1) Regeneration has been achieved by cutting portions of peripheral nerves of the hand or foot and autografting them into the central nerves. Thus, peripheral nerves presumably possess an environment which promotes regeneration of central nerves. Such studies began with research by Aguayo et al. in Canada in 1983[8].

2) As mentioned above, the central nerves themselves act to suppress neural regeneration. Reports have been published on the inhibiting effects of previously known myelin-related proteins, including Nogo factor which was described in 2000 in the journal Nature[9]. According to several reports, introducing antibodies against these factors to neutralize them can induce some degree of regeneration in the central nerves.

3) Regeneration is promoted by the following two types of cell transplantation.

a) Replenishment of degenerated neurons to reconstruct the neural network. This approach employs neuronal stem cells and embryonic neurons.

b) Reconstruction by transplantation of cells capable of inducing neural regeneration (glial cells), instead of replenishing the actual neurons. It has been attempted to use peripheral nerve-derived Schwann cells, central nerve-derived glial cells or central nerve-derived ependymal cells, having neurotrophic factors introduced, olfactory nerve-derived support cells, neuronal stem cells and the like.

Both methods have advantages and disadvantages, but as yet no revolutionary method has been developed.

The present inventors have for many years been involved in development of methods of neural regeneration and reestablishment of function. We have focused particularly on a method employing Schwann cells which support the tissue structure of peripheral nerves as described in 3)-b) above. Schwann cells are present in peripheral nerves, and it has been demonstrated that they are capable of inducing regeneration not only of their own peripheral nerve tissue but also of the central nervous system, that their transplantation at sites of injury provides a foothold for regenerating fibers and leads to effective neural regeneration, and that myelin which is responsible for neural saltatory transmission as an indispensable element for normal nerve functioning can also be reconstructed by transplantation of Schwann cells. It has also been confirmed in animal experiments that transplantation of Schwann cells leads to regeneration of cut optic nerves, (central nervous system).

Nevertheless, various difficulties are encountered when the relatively simple procedure of collecting and culturing Schwann cells in animal experiments is applied to humans. For example, since Schwann cells are present in the peripheral nerves, it is necessary to extract nerve samples from the hands or feet and isolate the cells, thereby leaving damage in the donor after extraction. As an additional difficulty, the limited proliferating ability of adult-derived Schwann cells requires a greater time period for large-scale culturing. Moreover, neural crest cells, which are believed to differentiate into Schwann cells, can only be extracted from embryonic peripheral nerves.

This situation has therefore necessitated provision of a natural Schwann cell substitute which can be used for neural regeneration treatment and can be obtained in large amounts by culturing.

Neuronal stem cells have been found in portions of the adult brain, and these differentiate into the neurons, astrocytes, oligodendrocytes, etc. of the nervous system (see FIG. 5). However, only a very minute number of such stem cells are present, and craniotomy is necessary to obtain them. In addition, recent research has shown, contrary to germ layer theory, that some types of cells may be able to differentiate into completely different types (see FIG. 6). As of the filing of the present application it has been known that bone marrow stromal cells are mesenchymal stem cells or precursor cells that not only carry out a hemopoietic support function but can themselves differentiate into osteoblasts, vascular endothelial cells, skeletal muscle cells, adipocytes, smooth muscle cells and the like[10]; nevertheless, no literature exists suggesting the possibility that bone marrow stromal cells might be capable of differentiating into neural crest cell-derived Schwann cells, nor has any method for such differentiation or induction been established.

In light of this situation, the present inventors have attempted experimentation and research on differentiation and induction to Schwann cells using bone marrow stromal cells instead of neural crest cells that are so difficult to obtain, as mentioned above. Bone marrow stromal cells are easy to extract by bone marrow puncture on an outpatient basis and have high proliferation potency, and thus allow large-scale culturing in a relatively short period of time.

DISCLOSURE OF THE INVENTION

As a result of repeated experimentation, the present inventors are the first to have succeeded in inducing differentiation of bone marrow stromal cells into Schwann cells with a high degree of efficiency by a multistage operation. Moreover, it was confirmed that actual regeneration and elongation of nerves occurred upon transplanting the bone marrow stromal cell-derived Schwann cells obtained by the differentiation inducing method into damaged optic nerves (central nervous system), and the present invention was thus completed.

The present invention therefore provides a method of inducing bone marrow stromal cells to differentiate into bone marrow stromal cell-derived Schwann cells in vitro, comprising the steps of:

(1) collecting bone marrow stromal cells from bone marrow and culturing the cells in a standard essential culture medium supplemented with a serum;

(2) adding a reducing agent to the culture medium and further culturing the cells;

(3) adding a differentiation inducing agent to the culture medium and further culturing the cells; and (4) adding a cyclic AMP-augmenting agent or a cyclic AMP analogue and/or a glial cell differentiation and survival stimulating factor to the culture medium, and further culturing the cells to obtain the bone marrow stromal cell-derived Schwann cells.

The invention further provides bone marrow stromal cell-derived Schwann cells obtained by the aforementioned method and a pharmaceutical composition for neural regeneration comprising the bone marrow stromal cell-derived Schwann cells. The invention still further provides a method of treating neural disease by transplanting the aforementioned bone marrow stromal cell-derived Schwann cells or a pharmaceutical composition for neural regeneration comprising them into a patient with neural disease to promote regeneration of the neural cells with which the disease is associated.

BRIEF DESCRIPTION OF THE DRAWINGS

FIG. 1a shows the state of a normal optic nerve, and FIG. 1b shows the state of an injured optic nerve.

FIG. 2 is an illustration of the structural differences between peripheral nerves and central nerves (including optic nerves).

FIG. 11 is a flow chart summary of the differentiation inducing method of the invention.

FIG. 13 is a pair of immunohistological confocal laser micrographs in lieu of a drawing, showing regeneration of an optic nerve after transplantation of bone marrow stromal cell-derived Schwann cells, using FITC, TexRed and Alexa633 as indicators.

FIG. 16 is a pair of immunohistological confocal laser micrographs in lieu of a drawing, showing regeneration of sciatic nerve after transplantation of bone marrow stromal cell-derived Schwann cells, using GFP, neurofilament and MAG.

FIG. 17 is another pair of immunohistological confocal laser micrographs in lieu of a drawing, showing regeneration of sciatic nerve after transplantation of bone marrow stromal cell-derived Schwann cells, using GFP, neurofilament and MAG.

FIG. 18 is another pair of immunohistological confocal laser micrographs in lieu of a drawing, showing regeneration of sciatic nerve after transplantation of bone marrow stromal cell-derived Schwann cells, using GFP, neurofilament and MAG.

DETAILED DESCRIPTION OF THE INVENTION

Figure 1:
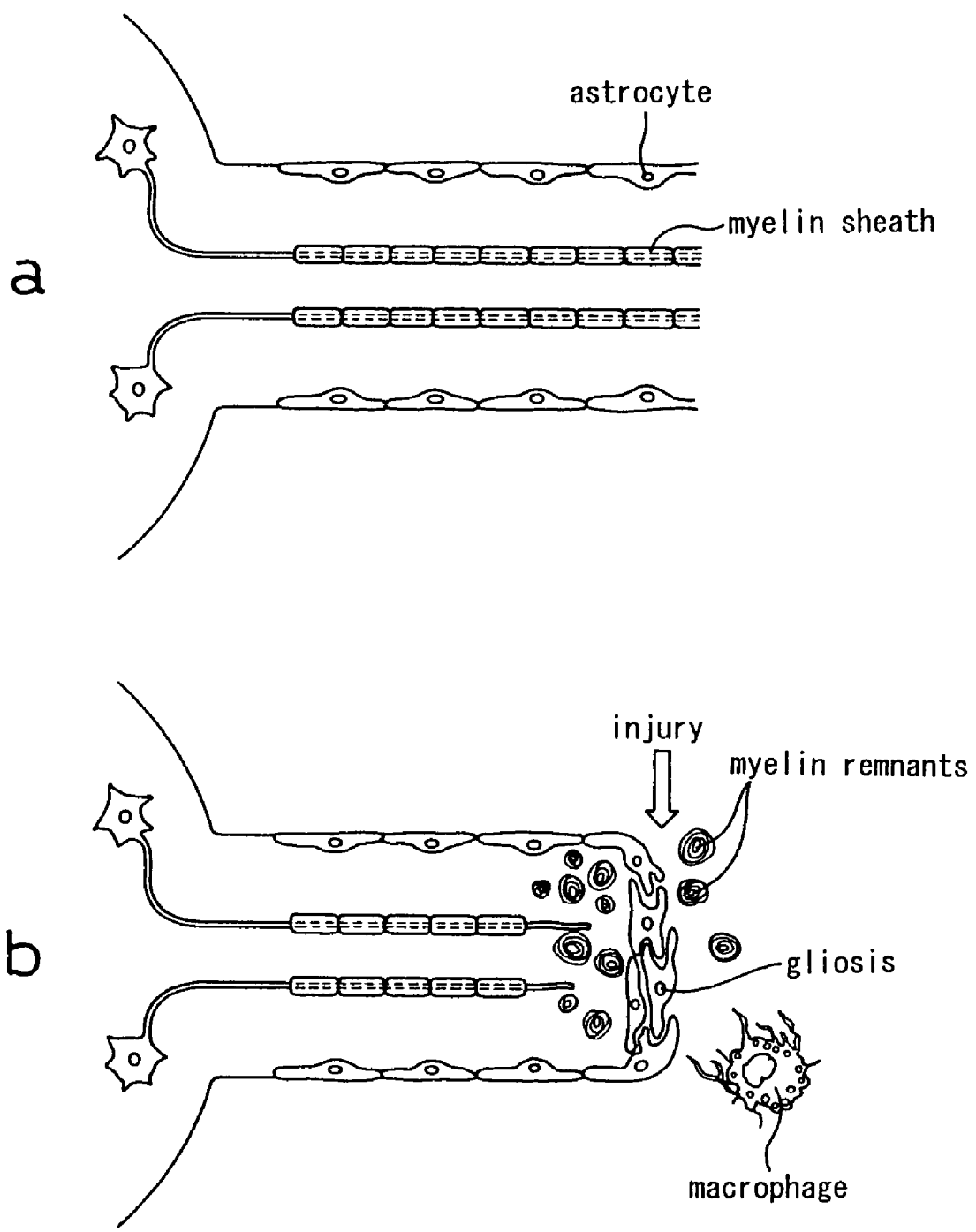
FIG. 1 is an illustration of the changes which occur in optic nerve glial cells after injury. Here.
Figure 3:
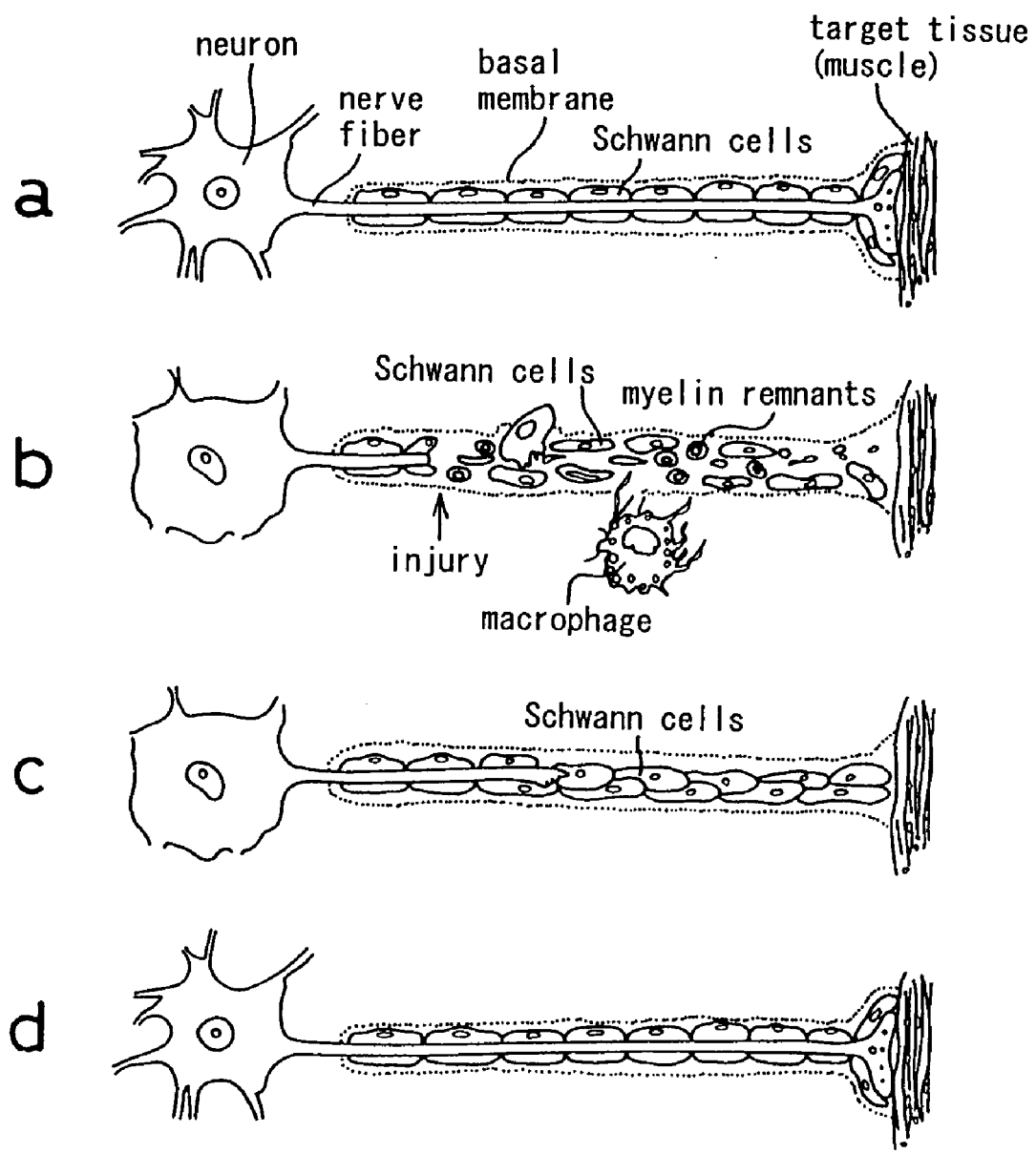
FIG. 3 is an illustration of Wallerian degeneration of a peripheral nerve. The normal nerve fiber is ensheathed by Schwann cells, and the exterior further covered by a continuous basal membrane (FIG. 3a). Upon injury, the peripheral end of the nerve fiber degenerates into myelin remnants which are processed by approaching macrophages (FIG. 3b), and after processing of the remains, activated Schwann cells proliferate inside the tube of the remaining basal membrane (FIG. 3c), leading to remyelination to complete the regenerated nerve fiber (FIG. 3d). ("Peripheral Nerve Injury and Repair", translation supervised by Y. Ikuta, Yodogawa Publications, FIG. 5.1 revised 1991.)
Figure 4:
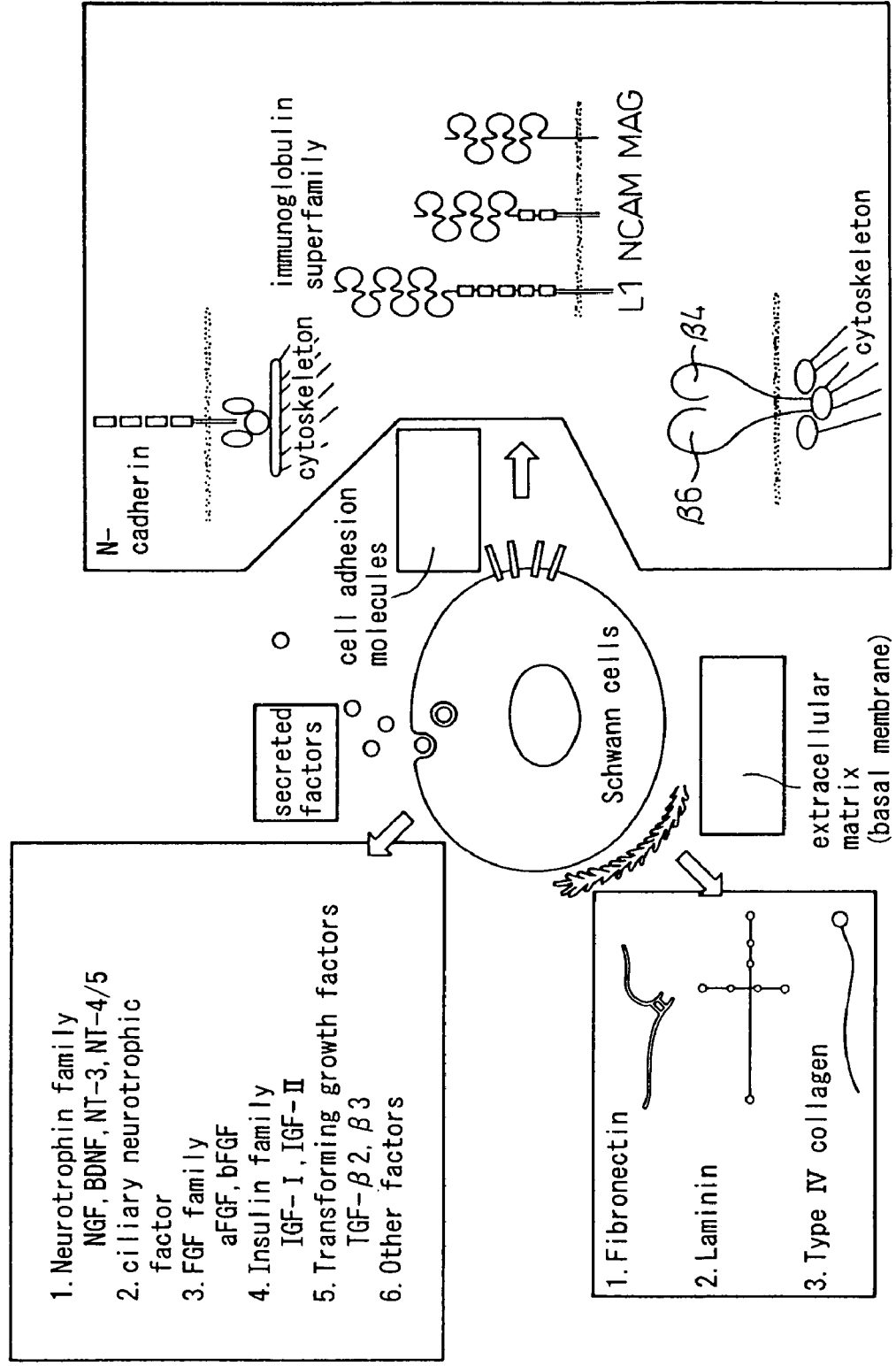
FIG. 4 is an graphical listing of neurotrophic factors associated with Schwann cells. Schwann cells produce secreted factors, extracellular matrix components and cell adhesion molecules, which work in concert for regeneration.
Figure 5:
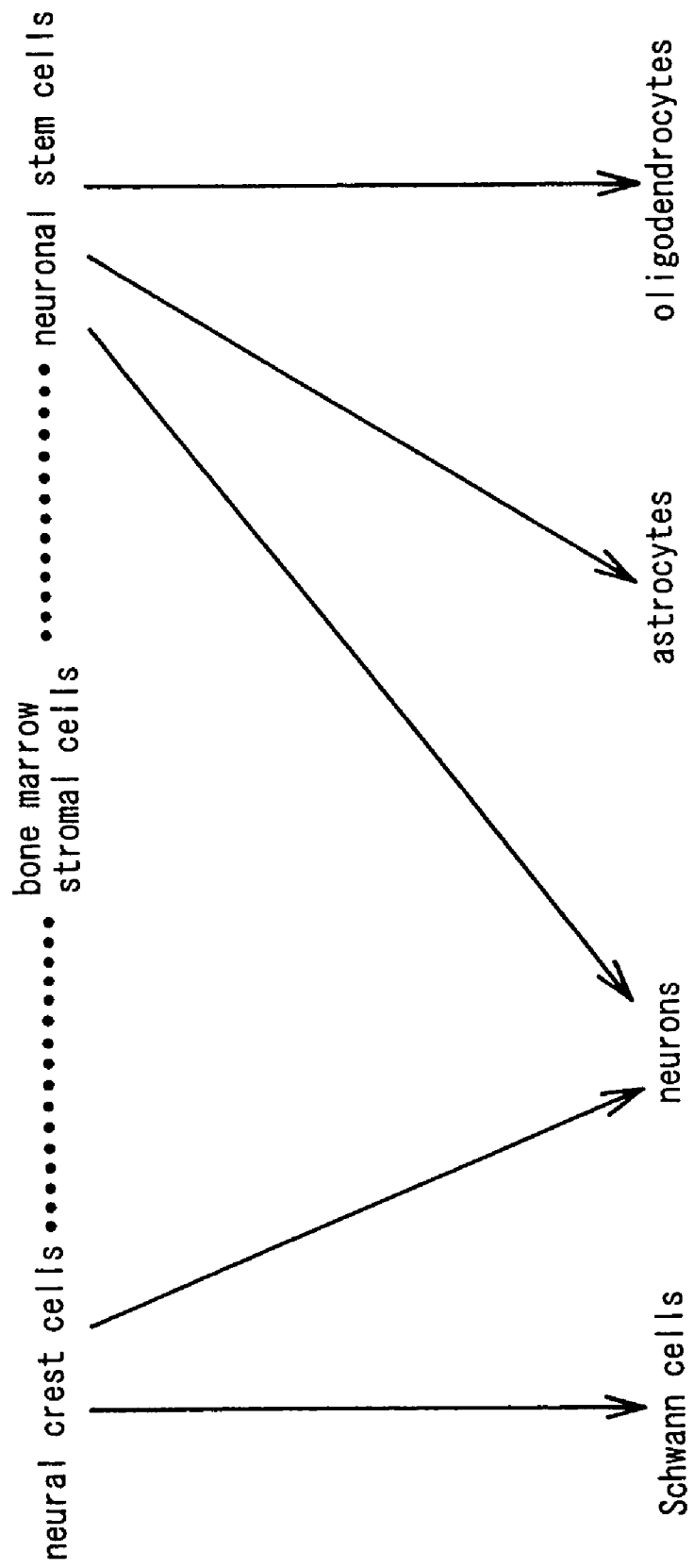
FIG. 5 is a schematic diagram for differentiation of neural cells.
Figure 6:
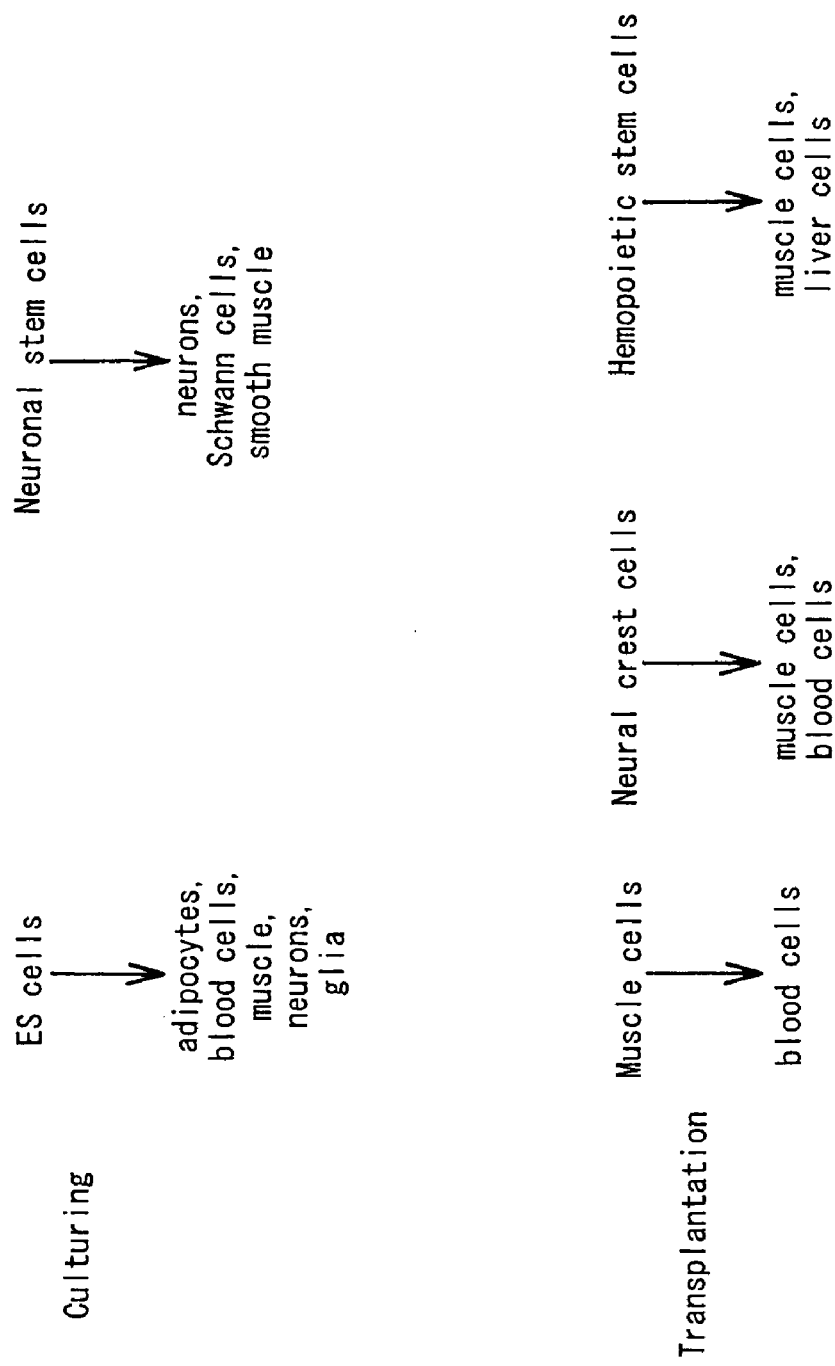
FIG. 6 is an illustration of differentiation whereby, contrary to germ layer theory, certain cells may be induced into completely different cell types.

According to one mode of the present invention there is provided a method of inducing bone marrow stromal cells to differentiate into bone marrow stromal cell-derived Schwann cells in vitro, comprising the steps of:

(1) collecting bone marrow stromal cells from bone marrow and culturing the cells in a standard essential culture medium supplemented with a serum;

(2) adding a reducing agent to the culture medium and further culturing the cells;

(3) adding a differentiation inducing agent to the culture medium and further culturing the cells; and (4) adding a cyclic AMP-augmenting agent or a cyclic AMP analogue and/or a glial cell differentiation and survival stimulating factor to the culture medium, and further culturing the cells to obtain the bone marrow stromal cell-derived Schwann cells.

The density of the cells in step (1) may be 50% confluency, and the cells are preferably subcultured to four generations.

The standard essential culture medium may be Minimum Essential Medium Eagle Alpha Modification (M4526, Sigma) and the serum may be fetal calf serum (14-501F, Lot #61-1012, BioWhittaker Co.). The serum may be added to a concentration of 20%. The reducing agent is an SH reagent, and the SH reagent is preferably β-mercaptoethanol (214-18, Lot# MOM7582, Nacalai Tesque). The concentration of the reducing agent may be 1 nM to 10 mM, preferably 10 nM to 5 mM and more preferably 100 μM to 2 mM. The culturing time in step (2) may be 1 hour to 5 days, preferably 12–48 hours and more preferably 18–30 hours. The aforementioned reagent concentration is the concentration in the culture medium with which the cells are in direct contact (same for reagents referred to hereunder).

The differentiation inducing agent may be retinoic acid (all-trans) (R-2625, Sigma). The differentiation inducing agent concentration may be 0.001 ng/ml to 1 μg/ml, preferably 1 ng/ml to 200 ng/ml and more preferably 10 ng/ml to 60 ng/ml. In step (3), the culture medium used in step (2) may be exchanged with fresh differentiation inducing agent-containing medium after step (2) has been completed. The fresh culture medium is identical to the culture medium used in step (1) except that it contains the differentiation inducing agent. The culturing time for step (3) may be 1 hour to 30 days, preferably 12 hours to 7 days and more preferably 2–4 days.

The cyclic AMP-augmenting agent or cyclic AMP analogue may be forskolin (344273, Calbiochem). The concentration of the cyclic AMP-augmenting agent or cyclic AMP analogue may be 0.001 ng/ml to 100 μg/ml, preferably 100 ng/ml to 50 μg/ml and more preferably 1 μg/ml to 10 μg/ml.

The glial cell differentiation and survival stimulating factor may be one selected from the group consisting of neuregulin, platelet-derived growth factor-AA (396-HB, Peprotech EC, Ltd.), basic fibroblast growth factor (100-18B, Peprotech EC, Ltd.) or mixtures thereof. Neuregulin is available as Heregulin™ (396-HB, R&D Corp.) The concentration of the glial cell differentiation and survival stimulating factor may be 0.001 ng/ml to 100 μg/ml, with a concentration of preferably 0.1 ng/ml to 100 ng/ml and more preferably 1 ng/ml to 10 ng/ml for platelet-derived growth factor-AA, and a concentration of preferably 10 ng/ml to 1 μg/ml and more preferably 100 ng/ml to 300 ng/ml for basic fibroblast growth factor. The culturing time in step (4) may be 1 hour to 30 days, and preferably 4 to 10 days.

According to another mode of the invention there are provided bone marrow stromal cell-derived Schwann cells obtained by the aforementioned differentiation inducing method.

According to yet another mode of the invention there is provided a pharmaceutical composition for neural regeneration comprising bone marrow stromal cell-derived Schwann cells.

According to yet another mode of the invention there is provided a method of treating neural disease by transplanting the aforementioned bone marrow stromal cell-derived Schwann cells or a pharmaceutical composition for neural regeneration comprising them into a patient with neural disease to cause regeneration of the neural cells with which the disease is associated.

Figure 7:
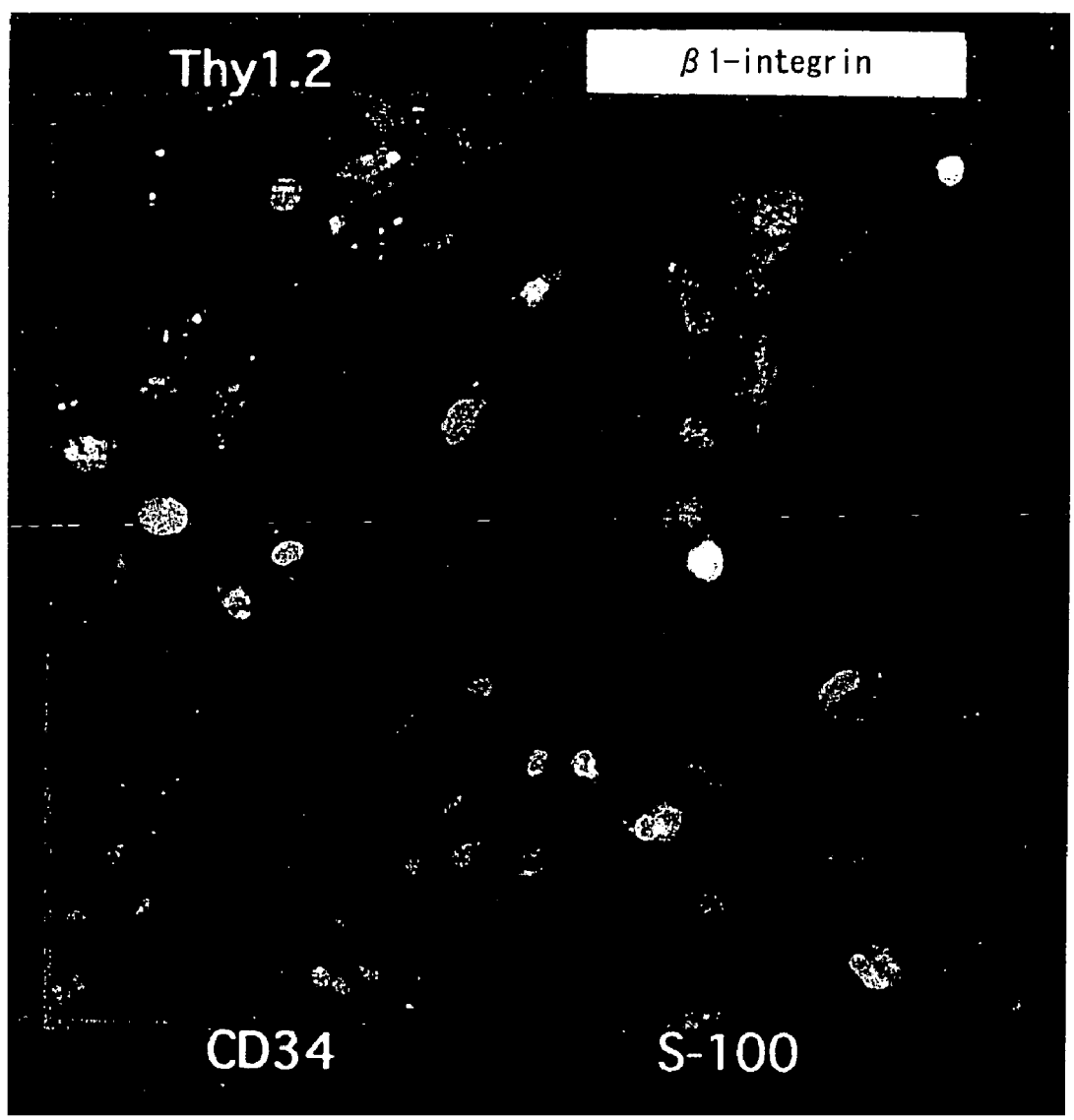
FIG. 7 is a composite of immunofluorescent photographs in lieu of a drawing, showing the features of bone marrow stromal cells before differentiation has been induced.

Throughout the present specification, the term "bone marrow stromal cells" refers to cells in the bone marrow which are not of the hemopoietic system and are considered capable of differentiating to cells of the bone, cartilage, etc. Bone marrow stromal cells are positive for Thy1.2 and (β1-integrin) and negative for CD34, as shown in the immunofluorescent photographs of FIG. 7. They may be positive or negative for S-100 (calcium-binding protein). Antibodies for Thy1.2, β1-integrin and CD34 were used.

Throughout the present specification, the term "natural Schwann cells" refers to Schwann cells collected from the peripheral nerves of living bodies, namely dorsal root ganglions. As seen in the upper immunofluorescent photograph of FIG. 8, they are positive for S-100.

Figure 8:
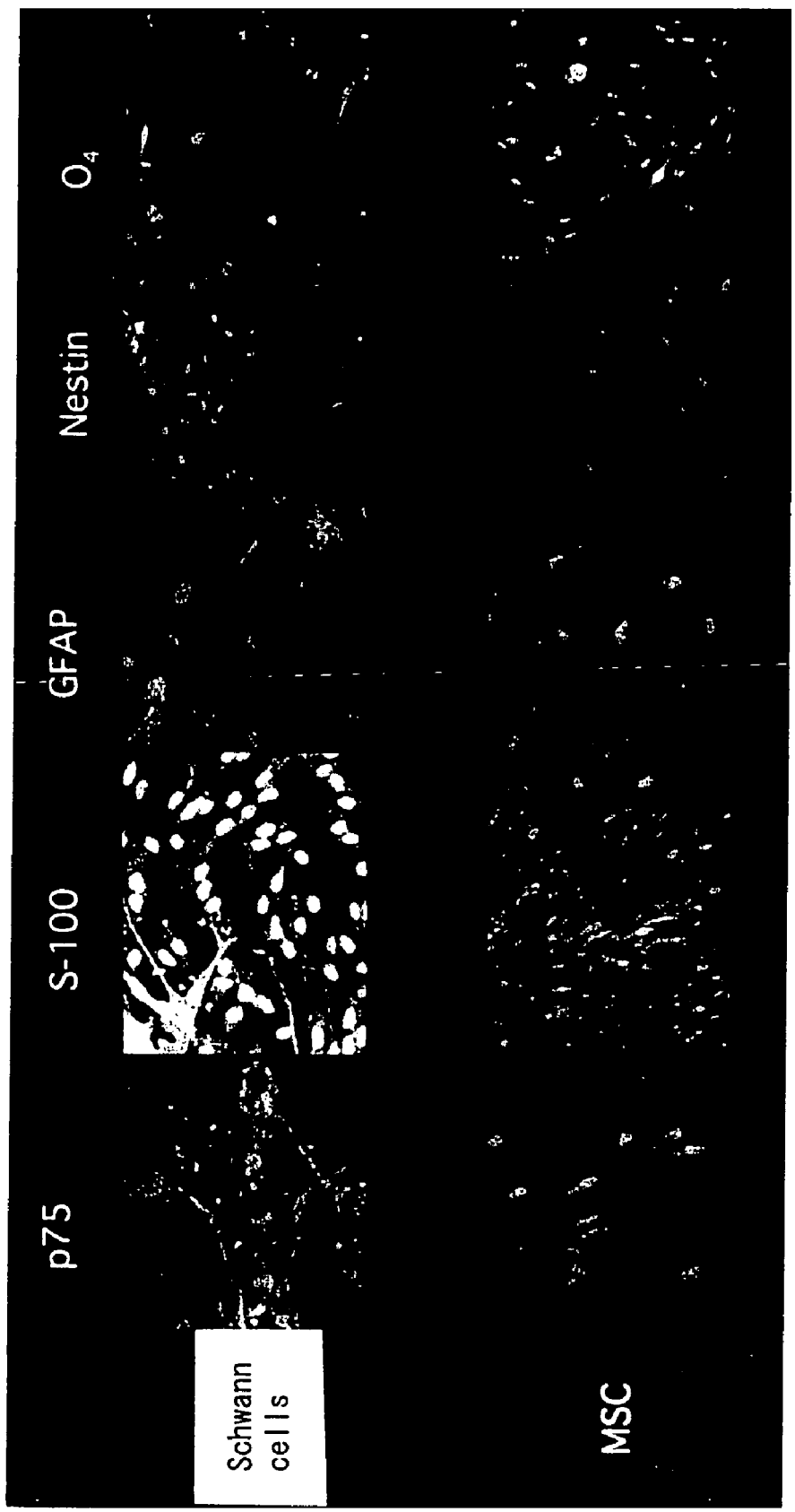
FIG. 8 is a composite of immunofluorescent photographs in lieu of a drawing, showing the features of bone marrow stromal cell-derived Schwann cells compared to natural Schwann cells.

Throughout the present specification, the term "bone marrow stromal cell-derived Schwann cells" refers to Schwann cells which (1) closely resemble natural Schwann cells in morphology and do not revert to the form of bone marrow stromal cells by subculturing, (2) exhibit the same reaction as Schwann cells with respect to P75 (nerve growth factor (NGF) receptor, low affinity), S-100, GFAP (glial fibrillary acidic protein, a type of intermediate filament), nestin (a type of intermediate filament) and O4 (a marker for myelin-producing cells such as Schwann cells and oligodendrocytes) based on immunostaining as shown in the lower immunofluorescent photographs of FIG. 8, and (3) have features similar to natural Schwann cells in their neurogenic ability, but can be distinguished from natural Schwann cells due to their distinct differentiation histories. Antibodies for P75, S-100, GFAP, nestin and O4 were obtained from the following sources: Anti-nerve growth factor-receptor, Boehringer Mannheim, 1198645; Anti-S-100, z-311, Dako Corp.; Anti-glial fibrillary acidic protein, L-1812, Dako Corp.; Anti-nestin, BMS4353, Bioproducts; Anti-O4, 1518925, Boehringer Mannheim.

Figure 9:
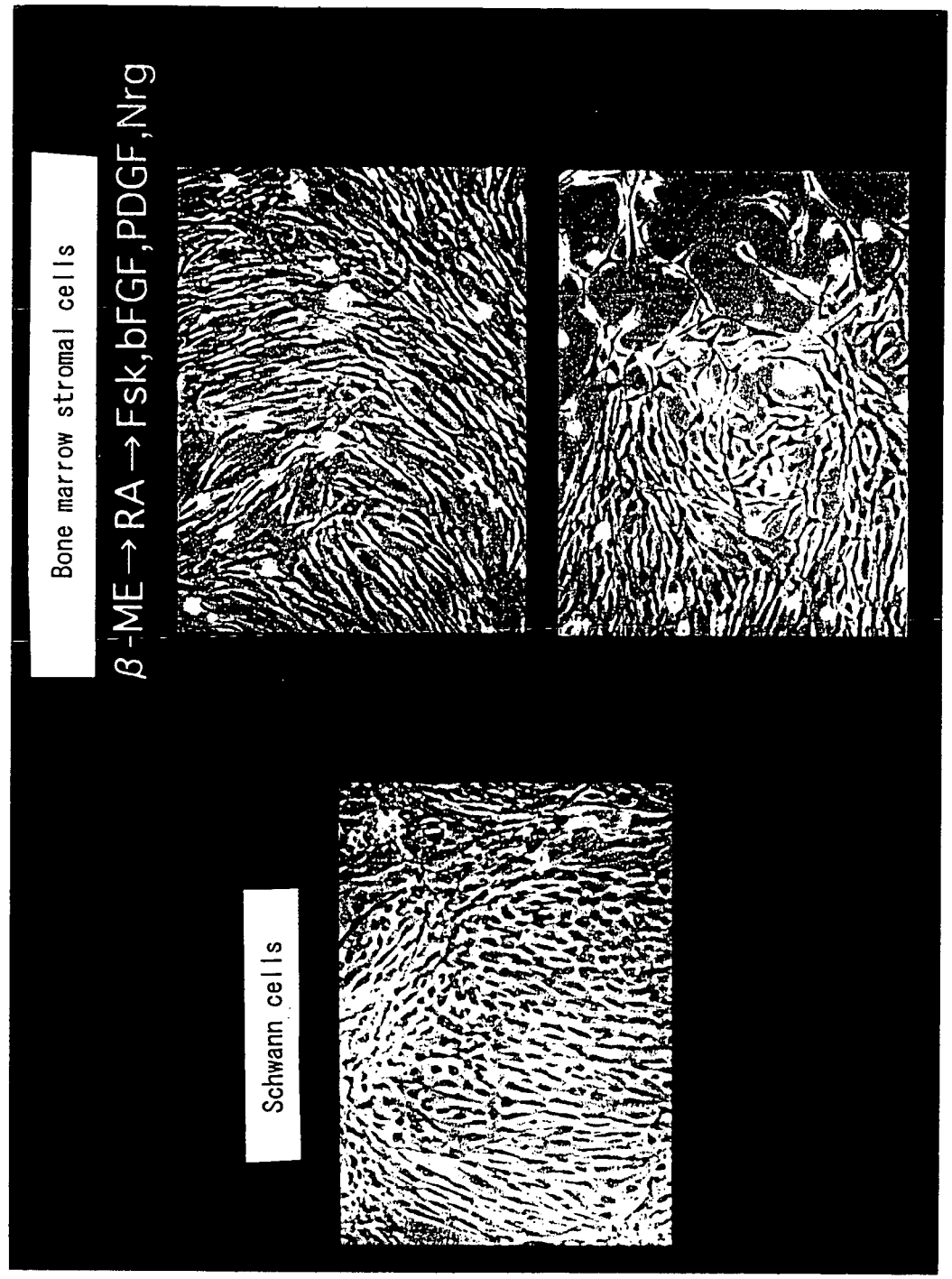
FIG. 9 is a composite of micrographs (phase contrast micrograph) in lieu of a drawing, showing the features of bone marrow stromal cell-derived Schwann cells obtained by the differentiation inducing method of the invention, compared to natural Schwann cells.

Bone marrow was treated in multistages according to the invention, as shown in the micrograph of FIG. 9.

Stromal cells (right upper and lower photographs in FIG. 9) exhibit the same morphology as natural Schwann cells (left photograph in FIG. 9).

Figure 10:
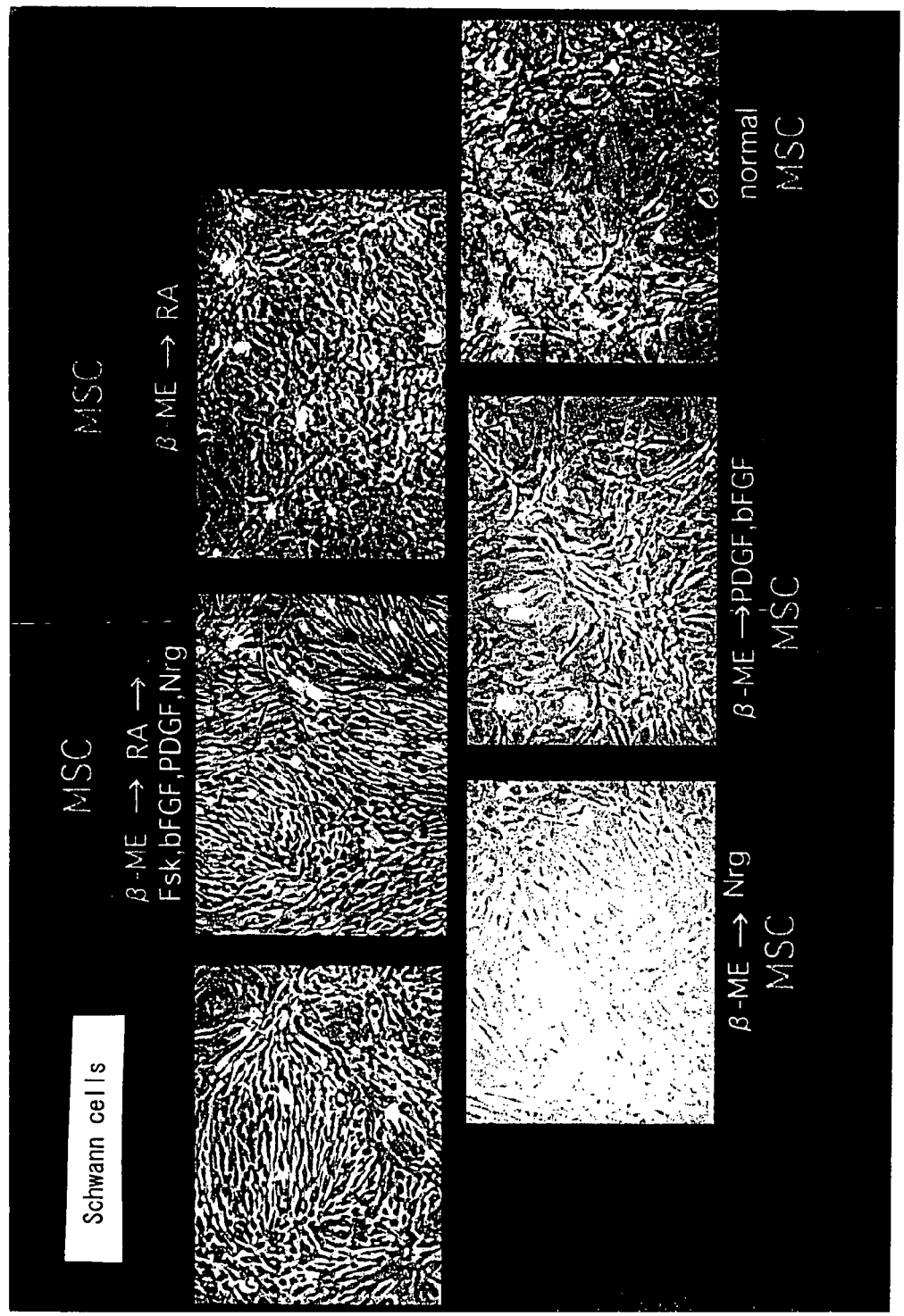
FIG. 10 is a composite of micrographs (phase contrast micrograph) in lieu of a drawing, showing the morphology of bone marrow stromal cell-derived Schwann cells obtained by the differentiation inducing method of the invention and cells obtained by the same method with some of the steps omitted, compared to natural Schwann cells and natural bone marrow stromal cells.

FIG. 10 shows the morphology of bone marrow stromal cells obtained by the method of inducing differentiation of bone marrow stromal cells according to the invention, without steps (2) to (4) or some of the reagents used therein. The micrograph at the upper left in FIG. 10 shows natural Schwann cells. The micrograph at the lower right shows bone marrow stromal cells before treatment. The top center micrograph shows results by the method of inducing differentiation of bone marrow stromal cells according to the invention conducted without omission of steps (2) to (4), and it is seen that the method of the invention produced cells exhibiting a morphology similar to natural Schwann cells. The micrograph at the upper right was obtained with omission of step (4), and the micrographs at the lower left and bottom center were taken without the differentiation inducing agent retinoic acid and without forskolin in step (3) and step (4), respectively.

It was thus demonstrated that the multistage treatment described in steps (2) to (4) above induces differentiation of bone marrow stromal cells into bone marrow stromal cell-derived Schwann cells with high efficiency.

The term "high efficiency" as used throughout the present specification means that the differentiation inducing method of the invention converts a high proportion of the original bone marrow stromal cells into the final bone marrow stromal cell-derived Schwann cells. The high efficiency of the differentiation inducing method of the invention is 50% or greater, preferably 75% or greater, more preferably 90% or greater and most preferably 95% or greater. Although each of the individual steps described above have been known, the selection and optimum combination of the steps as according to the present invention were first discovered by the present inventors, and the discovery is highly significant. Specifically, while it was known that bone marrow stromal cells are mesenchymal stem cells or precursor cells that are capable of being induced to differentiate into osteoblasts, vascular endothelial cells, skeletal muscle cells, adipocytes, smooth muscle cells and the like, as explained above, it was not known whether bone marrow stromal cells could actually be differentiated into neural crest cell-derived Schwann cells, and no party had successfully achieved this despite a strong desire to do so. The present inventors, though not wishing to be constrained by any theory, conjecture that the treatment with a reducing agent in step (2) produces a shock on the cells while the treatment with retinoic acid in step (3) resets the cells, after which the treatment with a cyclic AMP-augmenting agent or cyclic AMP analogue and a glial cell differentiation and survival stimulating factor in step (4) induces differentiation of the cells.

Bone marrow stromal cells may be collected and subjected to treatment involving multiple steps according to the present invention, to induce their differentiation into cells having the same features as natural Schwann cells with respect to neurogenic ability, with high efficiency. By transplanting the bone marrow stromal cell-derived Schwann cells into the peripheral and central nervous system, it has become possible to induce regeneration and elongation of injured nerves.

As explained above, the fact that natural Schwann cells must be collected from peripheral nerves presents a difficulty for application to humans. Bone marrow stromal cells, on the other hand, are easy to obtain without damaging the human body. Moreover, since the cells have a high rate of growth and can therefore be supplied rapidly in large amounts, the present invention makes possible a wider application of bone marrow stromal cells for a variety of nervous system disorders.

Another major advantage afforded by bone marrow stromal cells is their suitability for autologous transplantation. Collecting one's own bone marrow stromal cells, inducing them to differentiate and transplanting the differentiated cells into nerves produces no rejection reaction and therefore requires no immunosuppressants or the like, which should allow regeneration to be achieved in a more stable manner. Since bone marrow stromal cells can also be obtained from bone marrow banks, this method is also practical from the standpoint of supply.

As will be apparent by the examples provided below, the bone marrow stromal cell-derived Schwann cells of the present invention are considered widely applicable for regeneration of peripheral nerves or central nerves. According to one mode, therefore, the invention provides the bone marrow stromal cell-derived Schwann cells themselves. Due to their different induced differentiation histories as mentioned above, they are artificially modified cells which are distinct from natural Schwann cells. According to another mode, the invention provides the bone marrow stromal cell-derived Schwann cells in the form of a pharmaceutical composition for neural regeneration. The bone marrow stromal cell-derived Schwann cells of the invention are suitable for autologous transplantation as explained above, but they may also be allogenically transplanted. This is because the cells of the nervous system are not as susceptible to immune system attack, and rejection reaction can therefore be avoided by using donor cells with matching histocompatibility antigens from a bone marrow bank. The pharmaceutical composition may also contain common pharmaceutically acceptable carriers, buffers, salts, excipients and the like. The composition may be injected into the affected site directly or it may be filled into a hollow tube for transplantation at the site of a severed central or peripheral nerve.

Although peripheral nerves intrinsically are capable of regeneration, it is known that they cannot regenerate over gaps of several centimeters; such cases are also considered to be included among the practical applications to peripheral nerves.

Central nerve conditions wherein reconstruction is considered impossible encompass a wide gamut of different conditions, including injury-related spinal cord damage or cerebrovascular damage and diseases ranging from blinding glaucoma to degenerative diseases such as Parkinson's, which have a high estimated incidence rate among the population. The pharmaceutical composition of the invention may be used for regeneration of many and various types of central nerves. Research on methods of neural regeneration for the aforementioned conditions is an urgent social need, and the present invention is believed to have direct application for the human body.

The invention will now be explained in greater detail through the following examples, with the understanding that the examples are in no way limitative on the scope of the invention.

EXAMPLES

Example 1

Induced Differentiation of Bone Marrow Stromal Cells to Bone Marrow Stromal Cell-Derived Schwann Cells FIG. 11 is a flow chart summary of the treatment process for inducing differentiation.

Stromal cells were extracted from the bone marrow of adult rats (wistar rats) and cultured. The culture medium used was Minimum Essential Medium Eagle Alpha Modification supplemented with 20% fetal calf serum. After subculturing to four generations to reach 50% confluency, β-mercaptoethanol was added to a 1 mM concentration to the culture solution for a period of 24 hours. The medium was then exchanged with medium containing 35 ng/ml retinoic acid. The latter culture medium was also Minimum Essential Medium Eagle Alpha Modification supplemented with 20% fetal calf serum. After 3 days, the culture medium was again exchanged with medium containing 5 $\mu$M forskolin, 5 ng/ml platelet-derived growth factor-AA, 10 ng/ml basic fibroblast growth factor and 200 ng/ml Heregulin™. The cells were immunostained after 7 days. Based on reaction with antibodies for P75, O4, S-100, GFAP and nestin, the cells exhibited reactivities equivalent to natural Schwann cells (see FIG. 8). The bone marrow stromal cells had been induced to be morphologically similar to natural Schwann cells (see FIG. 9).

Example 2

Regeneration of Central Nerve (Severed Optic Nerve)

The cells obtained in Example 1 were collected by trypsin treatment and combined with mouse EHS tumor-derived Matrigel extracellular matrix (40234A, Collaborative Biomedical Products), and were then transplanted after being packed into artificial tubes (HIP10–43 Hollow fiber cartridge, Amicon) which were then sutured to severed optic nerves (central nervous system) of adult rats (Wistar).

Figure 12:
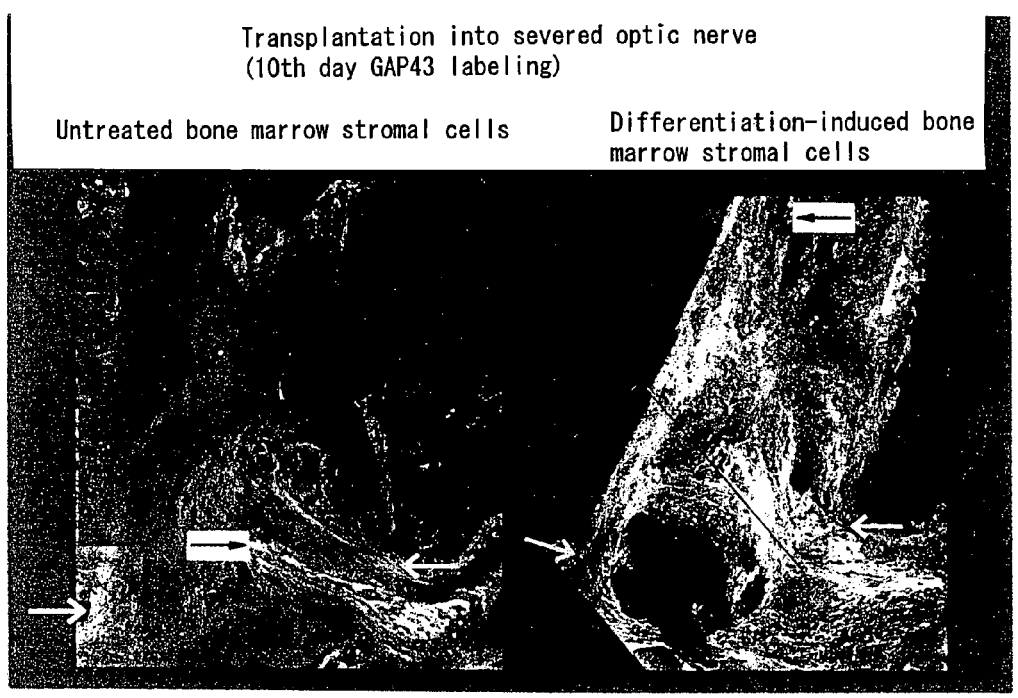
FIG. 12 is a pair of immunohistological confocal laser micrographs in lieu of a drawing, showing regeneration of an optic nerve after transplantation of bone marrow stromal cell-derived Schwann cells, using GAP43 as the indicator.

FIG. 12 shows the results with GAP43 (Growth Associated Protein-43, a protein expressed during growth and elongation of nerve fibers) labeling, 10 days after transplantation. The white arrows indicate the graft origins and the black arrows indicated the regenerating fiber tips. Significant elongation of nerve fibers is seen with the differentiation-induced bone marrow stromal cells (right) compared to the untreated bone marrow stromal cells (left). The nerve fiber elongation distance and number of fibers increased with the number of weeks.

The results at the third week after grafting are shown in FIG. 13. Here, FITC shown in grey is the immunohistological detection of anterograde labeled fibers obtained by injecting choleratoxin subunit B into the vitreous body in order to specifically label only the optic nerve fibers, and it shows regeneration of nerve fibers in the artificial tubes. TexRed shown in solid black represents the cultured bone marrow stromal cells pre-labeled with Brd-U. Alexa663 shown in dots represents MAG (Myelin-Associated Glycoprotein). Regeneration of the optic nerves was observed in the artificial tubes packed with bone marrow cells, and upon contacting these with the Brd-U labeled bone marrow stromal cells, formation of myelin was confirmed.

Example 3

Regeneration of Peripheral Nerve (Sciatic Nerve)

The sciatic nerves of adult rats (Wistar rats) were severed and inoculated with artificial tubes packed with differentiation-induced bone marrow stromal cells.

Figure 14:
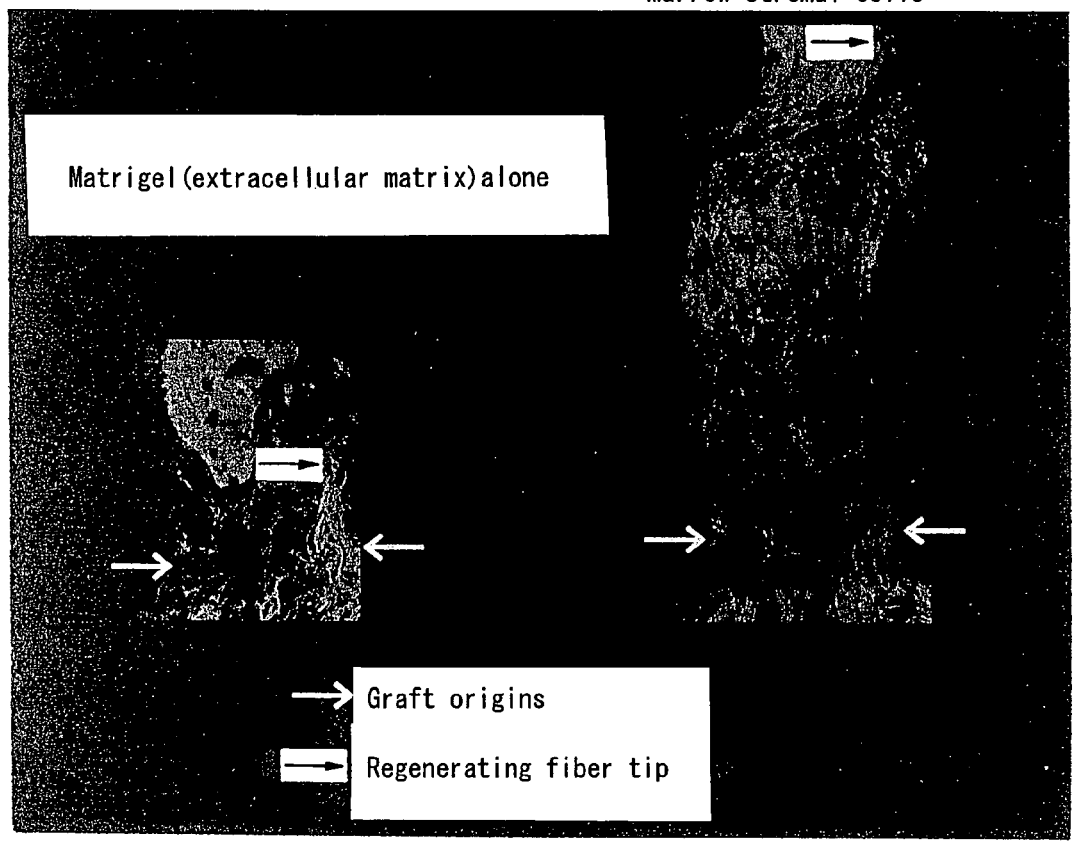
FIG. 14 is an immunohistological confocal laser micrograph in lieu of a drawing, showing regeneration of a sciatic nerve after transplantation of bone marrow stromal cell-derived Schwann cells, using GAP43 as the indicator.

FIG. 14 shows the results with GAP43 (Growth Associated Protein-43) labeling, 7 days after transplantation. The white arrows indicate the graft origins and the black arrows indicate the regenerating fiber tips. The nerve fibers are seen to be elongated with the differentiation-induced bone marrow stromal cells (right) compared to the Matrigel (extracellular matrix) alone (left). The nerve fiber elongation distance and number of fibers increased with the number of weeks.

Figure 15:
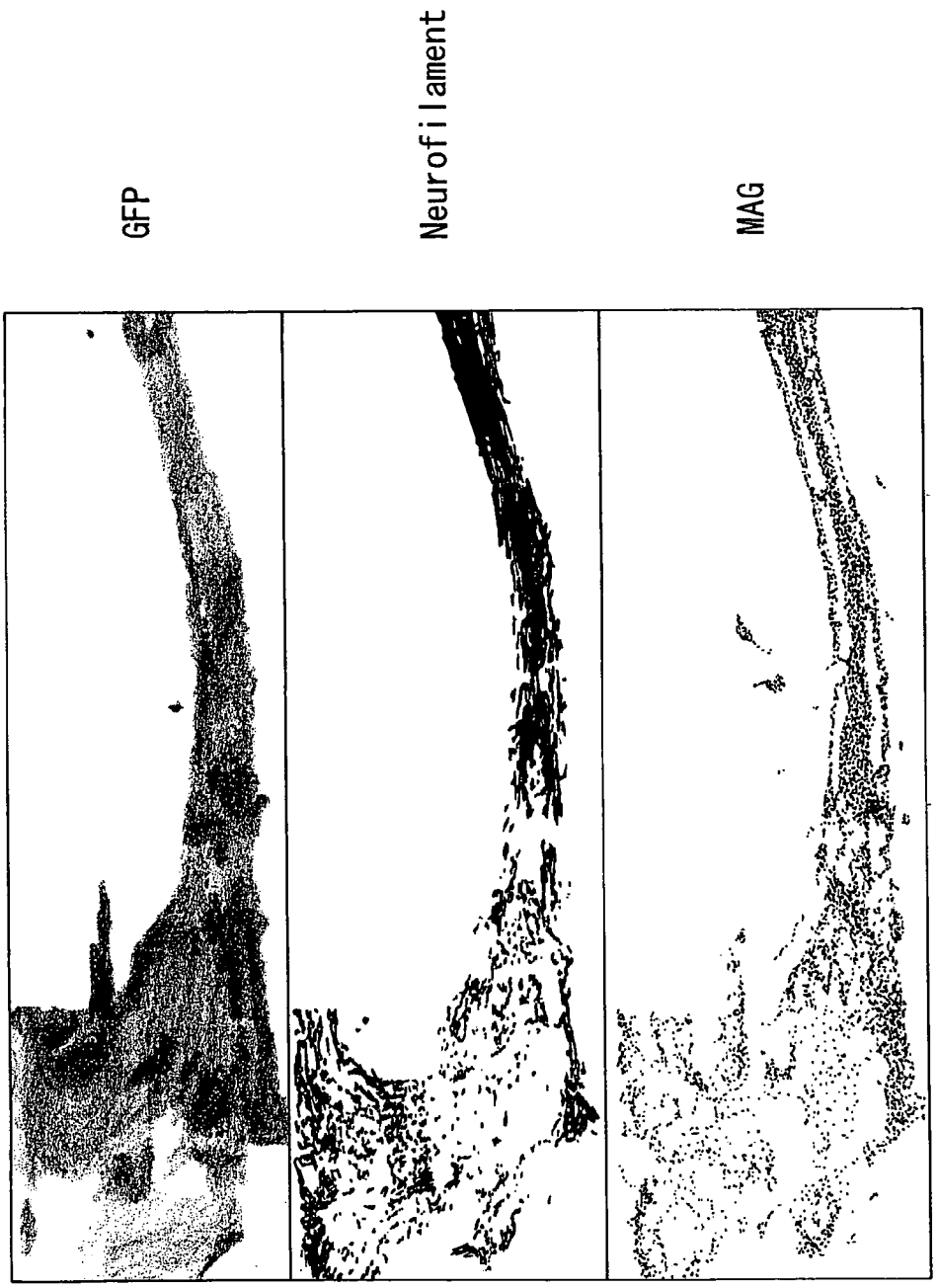
FIG. 15 is a set of immunohistological confocal laser micrographs in lieu of a drawing, showing regeneration of sciatic nerve after transplantation of bone marrow stromal cell-derived Schwann cells, using GFP, neurofilament and MAG.

The results at the fourth week after grafting are shown in FIG. 15. Here, GFP (Green Fluorescent Protein) shown in grey represents the bone marrow stromal cells illuminated by introducing the green fluorescent protein gene (GFP) using a retrovirus, MAG shown in dots represents myelin protein, and Neurofilament shown in red represents regenerated nerve fibers. FIG. 15 clearly shows excellent regeneration of the sciatic nerve by the fourth week after transplantation.

FIG. 16, FIG. 17 and FIG. 18 show the results of regeneration of sciatic nerves by the fourth week after transplantation. GFP shown in grey represents bone marrow stromal cells illuminated by introduction of the green fluorescent protein gene, MAG shown in dots represents detection of the myelin protein MAG using the fluorescent marker Alexa633, and Neurofilament shown in solid black represents regenerated nerve fibers detected using the red fluorescent marker Alexa 546. FIGS. 16 to 18 clearly indicate total regeneration of the sciatic nerves (peripheral nerves) by the fourth week after transplantation. That is, it is seen that the regenerated fibers (neurofilament) contacted with the bone marrow stromal cells illuminated green with GFP, and that the bone marrow stromal cells expressed the myelin protein MAG to form myelin.

REFERENCES

1. Schwab, M E et al: Rat CNS myelin and a subtype of oligodendrocytes in culture represent a nonpermissive substrate for neurite growth and fibroblast spreading. J Neurosci 8: 2381–2393, 1988

2. Hall, S et al: Electron microscopic study of the interaction of axons and glia at the site of anastomosis between the optic nerve and cellular or acellular sciatic nerve grafts. J Neurocytol 18: 171–184, 1989

3. Snow, D M et al: Sulfated proteoglycans in astroglial barriers inhibit neurite out-growth in vitro. Exp Neurobiol 109: 111–130, 1990

4. Blaugrund, E et al: Disappearance of astrocytes and invasion of macrophages following crush injury of adult rodent optic nerves: implications for regeneration. Exp Neurol 118: 105–115, 1992

5. Bastmeyer, M et al: Similarities and differences between fish oligodendrocytes and Schwann cells in vitro. Glia 11: 300–314, 1994

6. Vidal-Sanz, M et al: Axonal regeneration and synapse formation in the superior colliculus by retinal ganglion cells in the adult rat. J Neurosci 7: 2894–2909, 1987

7. Dezawa, M et al: The role of Schwann cells during retinal ganglion cell regeneration induced by peripheral nerve transplantation. Invest Ophthalmol Vis Sci 38: 1401–1410, 1997

8. Aguago, A. J. et al.; A potential for axonal regeneration in neurons of the adult mammalian nervous system. In Nervous System Regeneration, B. Haber, J. R. Perez-Polo, G. A. Hashim and A. M. G. Stella eds., pp. 327–340, Alan R. Liss, N.Y., 1983

9. Chen, M. S. et al.; Nogo-A is a myelin-associated neurite outgrowth inhibitor and an antigen for monoclonal antibody IN-1. Nature 403: 434–439, 2000

10. Taito, M., professor, Tohoku University), "Studies in establishing differentiation function-maintaining cell lines and using them for reconstruction of biohistological function", NEDO 1999 Teian Kobo Jigyo Seika Hokoku: 97S09-003.

What is claimed is:

1. A method of inducing bone marrow stromal cells to differentiate into bone marrow stromal cell-derived Schwann cells in vitro, comprising: (1) collecting bone marrow stromal cells from bone marrow, and culturing said cells in a standard essential culture medium supplemented with a serum (2) adding a reducing agent to said culture medium, and further culturing said cells; (3) adding retinoic acid to said culture medium, and further culturing said cells; and (4) adding forskolin, and/or a differentiation, survival and growth stimulating factor which acts on nerves and glial cells to said culture medium, and further culturing said cells to obtain said bone marrow stromal cell-derived Schwann cells.

2. The method as defined in claim 1, wherein said standard essential culture medium is an Eagle's alpha modified minimum essential medium.

3. The method as defined in claim 1, wherein said serum is fetal calf serum.

4. The method as defined in claim 1, wherein said reducing agent is sulfhydryl-containing reagents.

5. The method as defined in claim 4, wherein said sulfhydryl-containing is β-mercaptoethanol.

6. The method as defined in claim 1, wherein the concentration of said reducing agent is between 1 nM and 10 mM.

7. The method as defined in claim 1, wherein the culturing time in step (2) is between 1 hour and 5 days.

8. The method as defined in claim 1, wherein the concentration of said retinoic acid is between 0.001 ng/ml and 1 μg/ml.

9. The method as defined in claim 1, wherein the culturing time in step (3) is within 30 days.

10. The method as defined in claim 1, wherein the concentration of said forskolin is between 0.001 ng/ml and 100 μg/ml.

11. The method as defined in claim 1, wherein said glial cell differentiation and survival stimulating factor is selected from the group consisting of neuregulin, platelet-derived growth factor-AA, basic fibroblast growth factor, and mixtures thereof.

12. The method as defined in claim 11, wherein said neuregulin is Heregulin, a subtype of the same.

13. The method as defined in claim 1, wherein the concentration of said glial cell differentiation and survival stimulating factor is between 0.001 ng/ml and 100 μg/ml.

14. The method as defined in claim 1, wherein the culturing time in step (4) is within 30 days.

* * * * *